United States Patent [19]
Gall

[11] 3,992,400
[45] Nov. 16, 1976

[54] 1-(α-PHENYL-O-TOLYL)IMIDAZOLES

[75] Inventor: Martin Gall, Kalamazoo, Mich.

[73] Assignee: The Upjohn Company, Kalamazoo, Mich.

[22] Filed: Nov. 3, 1975

[21] Appl. No.: 628,571

Related U.S. Application Data

[62] Division of Ser. No. 565,107, April 4, 1974, Pat. No. 3,941,802.

[52] U.S. Cl. .............................................. 260/309
[51] Int. Cl.$^2$ ...................................... C07D 233/56
[58] Field of Search .................................. 260/309

[56] References Cited
UNITED STATES PATENTS

| | | | |
|---|---|---|---|
| 3,717,658 | 2/1973 | Metlesics et al. | 260/309.6 |
| 3,852,303 | 12/1974 | Houlihan | 260/309.6 |

Primary Examiner—Natalie Trousof
Attorney, Agent, or Firm—Hans L. Berneis

[57] ABSTRACT

Compounds of the formulae IV and V:

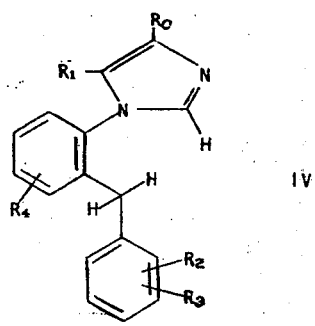

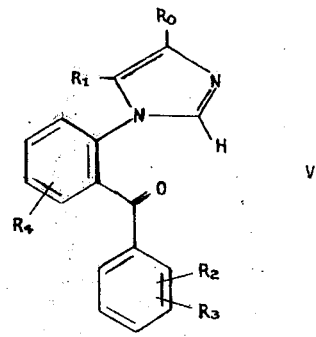

wherein $R_0$ and $R_1$ are hydrogen or alkyl of 1 to 3 carbon atoms, inclusive; wherein $R_2$ is hydrogen, fluoro, chloro, or trifluoromethyl; wherein $R_3$ is hydrogen or fluoro with the proviso that $R_3$ cannot be fluoro, if $R_2$ is chloro or trifluoromethyl; and wherein $R_4$ is hydrogen, fluoro, chloro, bromo, trifluoromethyl, or nitro, are obtained by a multi-step reaction from the corresponding α-(phenyl)-o-toluidine of the formula I:

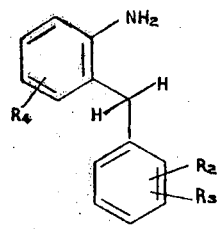

wherein $R_2$, $R_3$, and $R_4$ are defined as above, by treating I in sequence with an alkyl ester of orthoformic acid the resulting product with 2-alkyl-2-(aminoalkyl)-1,3-dioxolane or a 2-amino-alkanone dialkyl ketal and finally with titanium tetrachloride to obtain compound IV, and oxidizing compound IV to obtain the corresponding compound V.

Compounds IV and V have minor tranquilizing activity which can be utilized to calm mammals or birds. Their more important use, however, is as intermediates in the production of the strongly sedating and tranquilizing imidazolobenzodiazepines.

12 Claims, No Drawings

1-(α-PHENYL-o-TOLYL)IMIDAZOLES

This is a division of application Ser. No. 565,107, filed Apr. 4, 1974, now U.S. Pat. No. 3,941,802.

BRIEF SUMMARY OF THE INVENTION
FIELD OF THE INVENTION

This invention is directed to new organic compounds and more specifically to 1-(α-phenyl-o-tolyl)imidazoles and 2-(imidazol-1-yl)benzophenones and a process of the production therefor.

The new compounds and the process therefor is illustratively represented as follows:

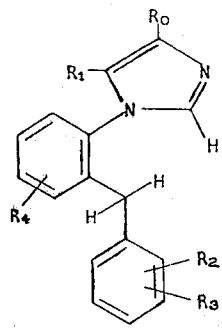
IV

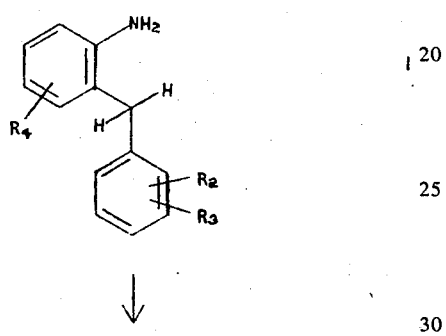
I

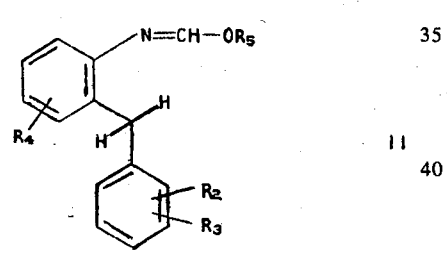
II

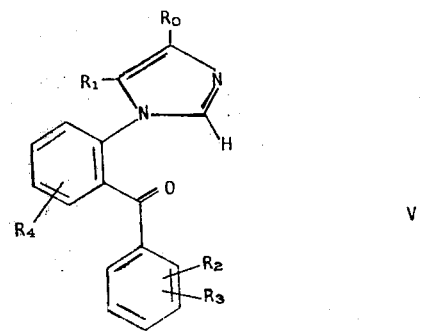
V

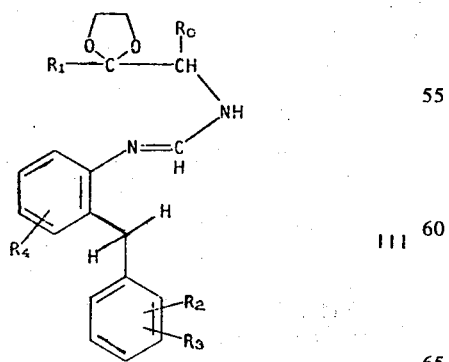
III wherein $R_o$ and $R_1$ are hydrogen or alkyl of 1 to 3 carbon atoms, inclusive; wherein $R_2$ is hydrogen, fluoro, chloro, or trifluoromethyl; wherein $R_3$ is hydrogen or fluoro with the proviso that $R_3$ is not fluoro if $R_2$ is chloro or trifluoromethyl; wherein $R_4$ is hydrogen, fluoro, chloro, bromo, trifluoromethyl, or nitro; and wherein $R_5$ is alkyl as defined above.

The process of this invention comprises: heating a compound of formula I with a trialkyl orthoformate wherein the alkyl group has from 1 to 3 carbon atoms, inclusive, with or without an inert organic solvent to obtain compound II; heating compound II in an inert organic solvent with an amino acetal or ketal VI

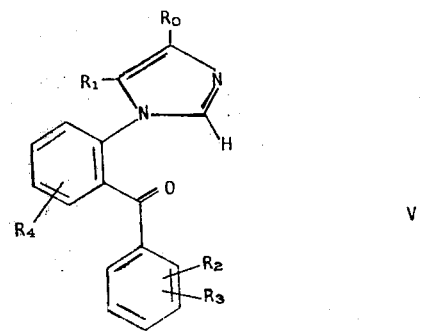
VI wherein $R_o$ and $R_1$ are defined as above to obtain compound III; treating at 0° to 20° C. compound III with titanium tetrachloride in an inert organic solvent and heating subsequently the mixture to reflux to obtain compound IV; oxidizing compound IV to obtain compound V.

Alternatively, compound II can be heated between 25° to 78° C. in a lower alkanol (1 to 3 carbon atoms) with an aminoaldehyde diacetal or aminoketone diketal of the formula VII:

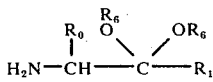
VII wherein $R_o$ and $R_1$ are defined as above and $R_6$ is methyl or ethyl to give the compound IIIA:

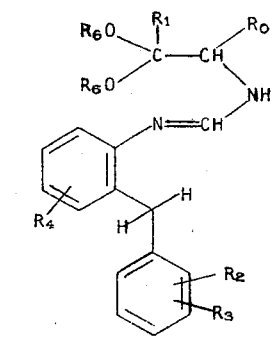

wherein $R_o$, $R_1$, $R_2$, $R_3$, $R_4$, and $R_6$ are defined as above. Compound IIIA is cyclized in the same manner as compound III with titanium tetrachloride.

DESCRIPTION OF THE PREFERRED EMBODIMENT

Lower alkyl groups of 1 to 3 carbon atoms, inclusive, are exemplified by methyl, ethyl, propyl, and isopropyl.

The more preferred compounds of this invention are of the formulae IVA and VA:

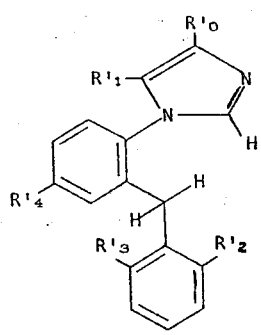
IVA and

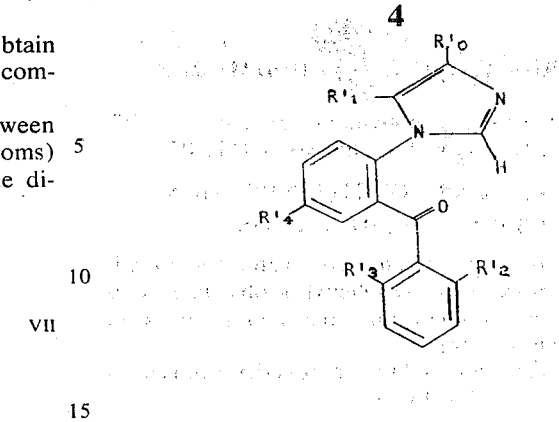
VA wherein $R'_o$ and $R'_1$ are hydrogen, methyl, or ethyl; wherein $R'_2$ is hydrogen, chloro, fluoro; wherein $R'_3$ is hydrogen or fluoro with the proviso that $R'_3$ is not fluoro, if $R'_2$ is chloro; and wherein $R'_4$ is hydrogen, fluoro, chloro, or trifluoromethyl.

The most preferred compounds of this invention are of the formula IVB and VB:

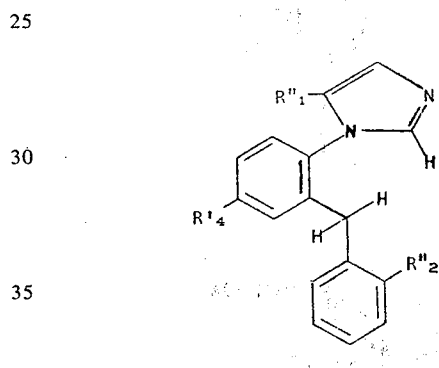
IVB and

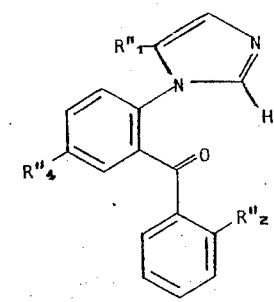
VB wherein $R''_1$ is hydrogen or methyl; wherein $R''_2$ is hydrogen or chloro; wherein $R''_4$ is hydrogen, chloro, or fluoro.

As tranquilizing agents, compounds of formulae IV or V can be used in unit dosage forms of 1 to 15 mg. per kg. and preferably in dosages of 1 to 10 mg./kg. In larger mammals, above 10 kg., the lower range of dosage is preferred.

As intermediates the compounds of formula V are first treated with formaldehyde in formalin to produce a 2-[(2-hydroxymethyl)imidazol-1-yl]benzophenone of the formula

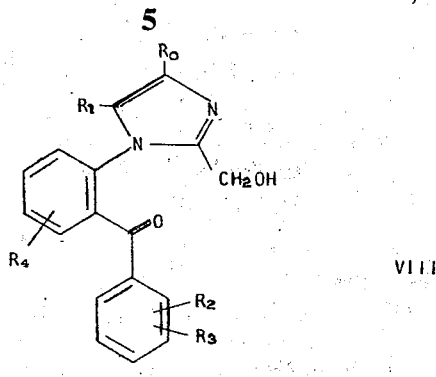

wherein $R_o$, $R_1$, $R_2$, $R_3$, and $R_4$ are defined as hereinbefore. Compound VIII is then treated e.g. with thionyl chloride to give the chloride of the alcohol VIII, and this compound is cyclized with ammonia to give the known end products 4H-imidazo[1,2-a] [1,4]benzodiazepines [Belgium Patent No. 787,251], which are important sedatives, hypnotics and tranquilizers.

The starting compounds of formula I of this invention are synthesized as shown in the Preparations.

The process of this invention comprises: heating a compound of formula I with an excess of a trialkyl orthoformate: In the preferred embodiment of this invention the solution of compound I in the orthoformate acid ester is refluxed for 5 to 24 hours. Trimethyl or triethyl orthoformate is preferred, but higher trialkyl orthoformates can be used. The refluxing is continued until most of the alcohol i.e. methanol or respectively ethanol is distilled. The resulting oil is the compound II which is used without further purification.

Compound II is dissolved in an inert organic solvent e.g. ethanol, methanol, propanol, and the solution is treated with an excess of 2-alkyl-2-(1-aminoalkyl)-1,3-dioxolane VI. The mixture is refluxed during ½ to 3 hours. Thereafter all volatile liquids are removed preferably by vacuum distillation, and the residue is purified by conventional means, such as washing with organic solvents, filtration, crystallization or the like to give the purified product of formula III.

Instead of using an amino compound of formula VI an aminoacetal or aminoketal of formula VII can be used. The reaction is usually carried out by reacting a solution of compound II in methanol or ethanol solution between 25° to 78° C. with compound VII for 1 to 24 hours to give the corresponding compound IIIA, which can be used without further purification.

Compound III in pure form or in the crude form is dissolved in an inert organic solvent and titanium tetrachloride is added. The addition is generally performed between 0° and 20° C. with stirring during 5 to 30 minutes. Thereafter the mixture is brought to reflux and kept at this temperature for 1 to 12 hours, to give the corresponding compound IV. Compound IV is isolated and purified by conventional methods e.g. extraction, filtering, chromatography, and crystallization.

Compound IV is oxidized to compound V with a chromic acid oxidizing agent.

In the preferred embodiment of this invention, the acetic acid solution of compound IV is admixed with Jones' reagent and the mixture is heated to reflux for 1 to 12 hours. After cooling the mixture is neutralized with a base, e.g. aqueous sodium or potassium hydroxide or carbonate, and the product V recovered by extraction. Conventional means, such as washing, filtering with or without filter aids, chromatography and/or crystallization are used to purify compound V.

The following preparations and examples are illustrative of the processes and products of the present invention, but are not to be construed as limiting.

PREPARATION 1

2-Amino-5-chlorobenzophenone hydrazone

A mixture of 27.2 g. (0.117 mol) of 2-amino-5-chlorobenzophenone in 170 ml. of diethylene glycol and 23 ml. (0.45 mol) of 99% hydrazine hydrate is brought to reflux for a total of 7 hours. The solution is allowed to cool overnight to room temperature. The light greencolored solid which results is mixed with 400 ml. of water and extracted into benzene; the layers are separated and the benzene portion dried over anhydrous magnesium sulfate and concentrated. Crystallization of the residue from ether/hexane gives 13.5 g. (46.8%) 2-amino-5-chlorobenzophenone hydrazone of melting point 133°–133.5° C.

Anal. calcd. for $C_{13}H_{12}ClN_3$: C, 63.55; H, 4.93; N, 17.11; Cl, 14.43. Found: C, 63.58; H, 4.95; N, 17.32; Cl, 14.39.

PREPARATION 2

2-Amino-2',5-dichlorobenzophenone hydrazone

In the manner given in Preparation 1, 2-amino-2',5-dichlorobenzophenone is refluxed with hydrazine hydrate in diethylene glycol to give 2-amino-2',5-dichlorobenzophenone hydrazine.

PREPARATION 3

2-Amino-5-chloro-2',6'-difluorobenzophenone hydrazone

In the manner given in Preparation 1, 2-amino-5-chloro-2',6'-difluorobenzophenone is refluxed with hydrazine hydrate in diethylene glycol to give 2-amino-5-chloro-2',6'-difluorobenzophenone hydrazone.

PREPARATION 4

2-Amino-2'-chloro-5-nitrobenzophenone hydrazone

In the manner given in Preparation 1, 2-amino-2'-chloro-5-nitrobenzophenone is refluxed with hydrazine hydrate in diethylene glycol to give 2-amino-2'-chloro-5-nitrobenzophenone hydrazone.

PREPARATION 5

2-Aminobenzophenone hydrazone

In the manner given in Preparation 1, 2-aminobenzophenone is refluxed with hydrazine hydrate in diethylene glycol to give 2-aminobenzophenone hydrazone.

PREPARATION 6

2-Amino-2'-chlorobenzophenone hydrazone

In the manner given in Preparation 1, 2-amino-2'-chlorobenzophenone is refluxed with hydrazine hydrate in diethylene glycol to give 2-amino-2'-chlorobenzophenone hydrazone.

PREPARATION 7

5-Fluoro-2-aminobenzophenone hydrazone

In the manner given in Preparation 1, 5-fluoro-2-aminobenzophenone is refluxed with hydrazine hydrate in diethylene glycol to give 5-fluoro-2-aminobenzophenone hydrazone.

PREPARATION 8

2-Amino-5-chloro-2'-fluorobenzophenone hydrazone

In the manner given in Preparation 1, 2-amino-5-chloro-2'-fluorobenzophenone is refluxed with hydrazine hydrate in diethylene glycol to give 2-amino-5-chloro-2'-fluorobenzophenone hydrazone.

PREPARATION 9

5-(Trifluoromethyl)-2-aminobenzophenone hydrazone

In the manner given in Preparation 1, 5-(trifluoromethyl)-2-aminobenzophenone is refluxed with hydrazine hydrate in diethylene glycol to give 5-trifluoromethyl-2-aminobenzophenone hydrazone.

PREPARATION 10

2-Amino-3'-chloro-5-nitrobenzophenone hydrazone

In the manner given in Preparation 1, 2-amino-3'-chloro-5-nitrobenzophenone is refluxed with hydrazine hydrate in diethylene glycol to give 2-amino-3'-chloro-5-nitrobenzophenone hydrazone.

PREPARATION 11

2-Benzyl-4-chloroaniline

Potassium hydroxide pellets (16.1 g. 287 mmol) are ground and dissolved in 85 ml. of refluxing diethylene glycol. Volatile materials are distilled until the temperature of the liquid reached 200° C. The solution is the cooled to room temperature and 13.5 g. (54.6 mmol) of 2-amino-5-chlorobenzophenone hydrazone is added while the syrupy liquid is gently reheated. At 100° C. all the hydrazone has dissolved. The temperature is maintained between 120°–150° C. for 45 minutes until gas evolution ceases. After a total heating period of 1.5 hours, the solution is cooled, poured onto ice and extracted with benzene. The benzene layer is separated, dried over anhydrous magnesium sulfate and concentrated to yield an orange oil. Distillation affords 9.9 g. of 2-benzyl-4-chloroaniline (89.2%) yellow oil of boiling point 125°–140° C. (at 0.1 mm Hg).

Anal. calcd. for $C_{13}H_{12}ClN$: C, 71.72; H, 5.56; N, 6.44; Cl, 16.28. Found: C, 71.55; H, 5.51; N, 6.58; Cl, 16.16.

PREPARATION 12

2-(o-Chlorobenzyl)-4-chloroaniline

In the manner given in Preparation 11, 2-amino-2',5-dichlorobenzophenone hydrazone is refluxed with potassium hydroxide in diethylene glycol to give 2-(o-chlorobenzyl)-4-chloroaniline, melting point 64°–65° C.

PREPARATION 13

4-Chloro-α-(2,6-difluorophenyl)-o-toluidine

In the manner given in Preparation 11, 2-amino-5-chloro-2',6'-difluorobenzophenone is refluxed with potassium hydroxide in diethylene glycol to give 4-chloro-α-(2,6-difluorophenyl)-o-toluidene.

PREPARATION 14

2-(o-Chlorobenzyl)-4-nitroaniline

In the manner given in Preparation 11, 2-amino-2'-chloro-5-nitrobenzophenone hydrazone is refluxed with potassium hydroxide in diethylene glycol to give 2-(o-chlorobenzyl)-4-nitroaniline.

PREPARATION 15

2-Benzylaniline

In the manner given in Preparation 11, 2-aminobenzophenone hydrazone is refluxed with potassium hydroxide in diethylene glycol to give 2-benzylaniline.

PREPARATION 16

2-(o-Chlorobenzyl)aniline

In the manner given in Preparation 11, 2-amino-2'-chlorobenzophenone hydrazone is refluxed with potassium hydroxide in diethylene glycol to give 2-(o-chlorobenzyl)aniline.

PREPARATION 17

4-Fluoro-α-(2,6-difluorophenyl)-o-toluidine

In the manner given in Preparation 11, 2-amino-2',5,6'-trifluorobenzophenone is refluxed with potassium hydroxide in diethylene glycol to give 4-fluoro-α-(2,6-difluorophenyl)-o-toluidene.

PREPARATION 18

2-(o-Fluorobenzyl)-4-chloroaniline

In the manner given in Preparation 11, 2-amino-2'-fluoro-5-chlorobenzophenone hydrazone is refluxed with potassium hydroxide in diethylene glycol to give 2-(o-fluorobenzyl)-4-chloroaniline.

PREPARATION 19

4-(Trifluoromethyl)-α-phenyl-o-toluidine

In the manner given in Preparation 11, 2-amino-5-(trifluoromethyl)benzophenone is refluxed with potassium hydroxide in diethylene glyclol to give 4-(trifluoromethyl)-α-phenyl-o-toluidine.

PREPARATION 20

2-Benzyl-4-nitroaniline

In the manner given in Preparation 11, 2-amino-5-nitrobenzophenone hydrazone is refluxed with potassium hydroxide in diethylene glycol to give 2-benzyl-4-nitroaniline.

In the manner given in the preceding preparations other α-phenyl-o-toluidine can be synthesized. Representative compounds thus obtained include:

2-(o-chlorobenzyl)-4-bromoaniline;
4-chloro-α-(m-chlorophenyl)-o-toluidine;
5-bromo-α-(o-fluorophenyl)o-toluidine;
4-bromo-α-phenyl-o-toluidine;
3-fluoro-α-(o-fluorophenyl)-o-toluidine;
3-(trifluoromethyl)-α-phenyl-o-toluidine;
5-nitro-α-[o-(trifluoromethyl)phenyl]-o-toluidine;
α-(o-fluorophenyl)-o-toluidine;
4-bromo-α-(o-chlorophenyl)-o-toluidine;
and the like.

EXAMPLE 1

1-(4-Chloro-α-phenyl-o-tolyl)imidazole

A. A solution of 50.6 g. [0.233 mmol] of 2-benzyl-4-chloroanilne and 82.85 g. [0.5095 mole] of triethyl orthoformate are kept at reflux during 5 hours. About 75 ml. of ethanol and other low boiling material are distilled leaving an oily residue.

B. The residual oil is then cooled to room temperature, dissolved in 500 ml. of reagent methanol and treated with 83.5 (0.795 mol) of aminoacetaldehyde, dimethyl acetal. The solution is refluxed for 3 hours until the imino ether has reacted completely.

C. The solvent is then removed in vacuo to give an oil which is dissolved in 1 liter of monoglyme. To this solution is carefully added 34.9 ml. of titanium tetrachloride (60.4 g., 0.318 mol). The solution turns brown immediately and warms considerably during the addition of the metal salt. The reaction mixture is stirred at ambient temperature for 10 minutes, then refluxed for 4 hours. It is permitted to cool overnight, then neutralized by pouring into 5.0 liter of cold aqueous 5% sodium hydroxide solution and extracting with chloroform (approximately 9 liter of solvent are used). The organic layers are washed with saturated aqueous sodium chloride, dried over anhydrous magnesium sulfate and concentrated to a syrup to give 51.6 g. of a black tarry substance. This is chromatographed over 2500 g. of silica gel and eluted with ethyl acetate, taking 1 liter fractions. The product is isolated in fractions 8 to 14 to give, after recrystallization from ether/hexane, 29.77 g. (48%) of colorless prisms of 1-(4-chloro-$\alpha$-phenyl-o-tolyl)imidazole of melting point 69°–70.5° C.

Anal. calcd. for $C_{16}H_{13}ClN_2$; mw. 268.72: C, 71.51; H, 4.87; N, 10.43; Cl, 13.19. Found: C, 71.81; H, 4.82; N, 10.42; Cl, 13.31.

EXAMPLE 2

1-[4-Chloro-$\alpha$-(o-chlorphenyl)-o-tolyl]-imidazole

A. 4-Chloro-$\alpha$-(o-chlorophenyl)-o-toluidine (58.7 g., 0.233 mol) is refluxed for 3 hours with 83.0 g. (0.509 mol) of triethyl orthoformate to remove ethanol leaving an oily residue.

B. This oily residue is cooled to room temperature, dissolved in 500 ml. of methanol and treated with 83.5 g. (0.795 mol) of amino acetaldehyde, dimethylacetal. The solution is stirred at room temperature for 20 minutes and then refluxed for 3½ hours.

C. The solvent is removed in vacuo and the resulting oil, dissolved in 1 l. of monoglyme, is treated cautiously with 34.9 ml. (60.4 g., 0.318 mol) of reagent titanium tetrachloride. The reaction mixture is stirred at ambient temperature for 10 minutes, then refluxed for 4 hours, cooled to room temperature, poured on to ice and neutralized with 5.0 l. of cold 10% aqueous sodium hydroxide solution. The mixture is treated with chloroform and both layers are filtered through Celite to remove suspended solids. The layers are separated and the aqueous layer is extracted thoroughly with methylene chloride. The combined organic layers are washed with brine, dried over anhydrous magnesium sulfate and concentrated in vacuo to an oil (140.0 g.) which is chromatographed over 4.8 kg. of silica gel by eluting with 30% ethyl acetate/70% Skellysolve B hexane mixtures and taking 600 ml. fractions. After the 20th fraction the column is eluted with a 50% ethyl acetate/Skellysolve B hexane mixture. The product is isolated in fractions 21–29 and crystallized from ethyl acetate to afford 18.43 g. of 1-[4-chloro-$\alpha$-(o-chlorophenyl)-o-tolyl]imidazole of melting point 62°–63° C. An analytical sample has a melting point 63.5°–64.5° C.

Anal. calcd. for $C_{16}H_{12}Cl_2N_2$, mw 303.19: C, 63.38; H, 3.99; N, 9.24; Cl, 23.39. Found: C, 63.15; H, 3.94; N, 9.19; Cl, 23.18.

EXAMPLE 3

5-Methyl-1-(4-chloro-$\alpha$-phenyl-o-tolyl)-imidazole

A. N'-(4-Chloro-$\alpha$-phenyl-o-tolyl)-N-[(2-methyl-1,3-dioxolan-2-yl)methyl]formalidine A solution of 5.06 g. (23.3 mmol) of 2-benzyl-4-chloroaniline and 8.28 g. (51.0 mol) of triethyl orthoformate is refluxed for 5 hours to distill ethanol. The resulting yellow oil is dissolved in 25 ml. of absolute ethanol, treated with 2-methyl-2-(aminomethyl)-1,3-dioxolane and heated for 1.5 hours at reflux. All the volatile liquids are removed in vacuo to afford 5.26 g. of N'-(4-chloro-$\alpha$-phenyl-o-tolyl)-N-[(2-methyl-1,3-dioxolan-2-yl)-methyl]formalidine which is filtered and washed with hexane. The analytical sample recrystallized from ethyl acetate/hexane has a melting point of 105°–107° C.

Anal. calcd. for $C_{19}H_{21}ClN_2O_2$, mw 344.83: C, 66.17; H, 6.14; N, 8.13; Cl, 10.28; Found: C, 65.98; H, 6.12; N, 8.03; Cl, 10.35.

B. 5-Methyl-1-(4-chloro-$\alpha$-phenyl-o-tolyl)imidazole

The product from A (2.77 g., 8.11 mol) is dissolved in 40 ml. of monoglyme and treated carefully at room temperature with 1.22 ml. (2.10 g., 11.1 mmol) of reagent titanium tetrachloride. After the initial vigorous exothermic reaction has subsided, the reaction mixture is heated to reflux on a steam bath for 3 hours. The reaction mixture is quenched on ice, neutralized, extracted with chloroform, dried and chromatographed over 150 g. of silica gel by eluting with 100 ml. of ethyl acetate and 900 ml. of a 1/99 methanol/ethyl acetate mixture (18 ml. fractions are collected). The product is collected in fractions 24–37 and crystallized from ethyl acetate/hexane mixtures to afford 0.71 g. of 5-methyl-1-(4-chloro-$\alpha$-phenyl-o-tolyl)imidazole of melting point 64°–66° C. A second crop weighs 0.17 g. The analytical sample, crystallized from ethyl acetate/hexane mixtures, has a melting point of 65°–66° C.

Anal. calcd. for $C_{17}H_{15}ClN_2$, mw 282.76: C, 72.21; H, 5.35; N, 9.91; Cl, 12.54. Found: C, 71.97; H, 5.38; N, 9.79; Cl, 12.85.

EXAMPLE 4

[1-$\lambda$4-Nitro-$\alpha$-(o-chlorophenyl)-o-tolyl]-imidazole

In the manner given in Example 1, 4-nitro-$\alpha$-(o-chlorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-nitro-$\alpha$-(o-chlorophenyl)-o-tolyl]imidazole.

EXAMPLE 5

5-Methyl-1-[4-nitro-$\alpha$-(o-chlorophenyl)-o-tolyl]imidazole

In the manner given in Example 3, 4-nitro-$\alpha$-(o-chlorophenyl)-o-toluidine is reacted with triethyl orthoformate. The resulting oil is heated with 2-methyl-2-(aminomethyl)-1,3-dioxolane, and the resulting product treated with titanium tetrachloride to give 5-methyl-1-[4-nitro-$\alpha$-(o-chlorophenyl)-o-tolyl]imidazole.

EXAMPLE 6

1-[4-Fluoro-$\alpha$-(o-chlorophenyl)-o-tolyl]imidazole

In the manner given in Example 1, 4-fluoro-$\alpha$-(o-chlorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-fluoro-α-(o-chlorophenyl)-o-tolyl]imidazole.

EXAMPLE 7

5-Ethyl-1-[4-fluoro-α-(o-chlorophenyl)-o-tolyl-]imidazole

In the manner given in Example 3, 4-fluoro-α-(o-chlorophenyl)-o-toluidine is reacted with triethyl orthoformate, the resulting oil is heated with 2-ethyl-2-(aminomethyl)-1,3-dioxolane, and the resulting product is treated with titanium tetrachloride to give 5-ethyl-1-[4-fluoro-α-(o-chlorophenyl)-o-tolyl-]imidazole.

EXAMPLE 8

1-[4-(Trifluoromethyl)-α-phenyl-o-tolyl]imidazole

In the manner given in Example 1, 4-(trifluoromethyl)-α-phenyl-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[(4-trifluoromethyl)-α-phenyl-o-tolyl]imidazole.

EXAMPLE 9

5-Methyl-1-[4-(trifluoromethyl)-α-phenyl-o-tolyl-]imidazole

In the manner given in Example 3, 4-(trifluoromethyl)-α-phenyl-o-toluidine is reacted with triethyl orthoformate, the resulting oil is heated with 2-methyl-2-(aminomethyl)-1,3-dioxolane, and the resulting product treated with titanium tetrachloride to give 5-methyl-1-[(4-trifluoromethyl)-α-phenyl-o-tolyl]imidazole.

EXAMPLE 10

1-[4-Chloro-α-(2,6-difluorophenyl)-o-tolyl]imidazole

In the manner given in Example 1, 4-chloro-α-(2,6-difluorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-chloro-α-(2,6-difluorophenyl)-o-tolyl]imidazole.

EXAMPLE 11

4-Ethyl-5-methyl-1-[4-chloro-α-(2,6-difluorophenyl)-o-tolyl]imidazole

In the manner given in Example 3, 4-chloro-α-(2,6-difluorophenyl)-o-toluidine is reacted with triethyl orthoformate, the resulting oil is heated with 2-methyl-2-(1-aminopropyl)-1,3-dioxolane, and the resulting product is treated with titanium tetrachloride to give 4-ethyl-5-methyl-1-[4-chloro-α-(2,6-difluorophenyl)-o-tolyl]imidazole.

EXAMPLE 12

1-(4-Nitro-α-phenyl-o-tolyl)imidazole

In the manner given in Example 1, 4-nitro-α-phenyl-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-nitro-α-phenyl-o-tolyl]imidazole.

EXAMPLE 13

5-Methyl-1-(4-nitro-α-phenyl-o-tolyl)imidazole

In the manner given in Example 3, 4-nitro-α-phenyl-o-toluidine is reacted with triethyl orthoformate, the resulting oil is heated with 2-methyl-2-(aminomethyl)-1,3-dioxolane, and the resulting product treated with titanium tetrachloride to give 5-methyl-1-(4-nitro-α-phenyl-o-tolyl)imidazole.

EXAMPLE 14

1-(4-Fluoro-α-phenyl-o-tolyl)imidazole

In the manner given in Example 1, 4-fluoro-α-phenyl-o-toluidine is reacted first with trimethyl orthoformate; the resulting product is reacted with aminoacetaldehyde, dimethyl acetal, and the resulting product of this reaction is heated with titanium tetrachloride in monoglyme to give 1-(4-fluoro-α-phenyl-o-tolyl)imidazole.

EXAMPLE 15

5-Methyl-1-(4-chloro-α-(o-chlorophenyl)-o-tolyl)imidazole

In the manner given in Example 3, 4-chloro-α-(o-chlorophenyl)-o-toluidine is reacted with triethyl orthoformate, the resulting oil is heated with 2-methyl-2-(aminomethyl)-1,3-dioxolane, and the resulting product treated with titanium tetrachloride to give 5-methyl-1-[4-chloro-α-(o-chlorophenyl)-o-tolyl]imidazole.

EXAMPLE 16

1-(α-Phenyl-o-tolyl)imidazole

In the manner given in Example 1, α-phenyl-o-toluidine is reacted first with trimethyl orthoformate; the resulting product is reacted with aminoacetaldehyde, dimethyl acetal, and the resulting product of this reaction is heated with titanium tetrachloride in monoglyme to give 1-(α-phenyl-o-tolyl)imidazole.

EXAMPLE 17

5-Methyl-1-(α-phenyl-o-tolyl)imidazole

In the manner given in Example 3, α-phenyl-o-toluidine is reacted with triethyl orthoformate, the resulting oil is heated with 2-methyl-2-(aminomethyl)-1,3-dioxolane, and the resulting product treated with titanium tetrachloride to give 5-methyl-1-(α-phenyl-o-tolyl)imidazole.

EXAMPLE 18

1-[4-chloro-α-(o-fluorophenyl)-o-tolyl]imidazole

In the manner given in Example 1, 4-chloro-α-(o-fluorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-chloro-α-(o-fluorophenyl)-o-tolyl]imidazole.

EXAMPLE 19

5-Methyl-1-[α-(o-chlorophenyl)-o-tolyl]imidazole

In the manner given in Example 3, α-(o-chlorophenyl)-o-toluidine is reacted with triethyl orthoformate, the resulting oil is heated with 2-methyl-2-(aminomethyl)-1,3-dioxolane, and the resulting product treated with titanium tetrachloride to give 5-methyl-1-[α-(o-chlorophenyl)-o-tolyl]imidazole.

EXAMPLE 20

1-[α-(o-chlorophenyl)-o-tolyl]imidazole

In the manner given in Example 1, α-(o-chlorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[α-(o-chlorophenyl)-o-tolyl]imidazole.

EXAMPLE 21

4,5-Diethyl-1-[α-(o-fluorophenyl)-o-tolyl]imidazole

In the manner given in Example 3, α-(o-fluorophenyl)-o-toluidine is reacted with triethyl orthoformate, the resulting oil is heated with 2-ethyl-2-(1-aminopropyl)-1,3-dioxolane, and the resulting product treated with titanium tetrachloride to give 4,5-diethyl-1-[α-(o-fluorophenyl)-o-tolyl]imidazole.

EXAMPLE 22

1-[4-Bromo-α-(o-chlorophenyl)-o-tolyl]imidazole

In the manner given in Example 1, 4-bromo-α-(o-chlorophenyl)-o-toluidine is reacted first with trimethylorthoformate; the resulting product is reacted with aminoacetaldehyde, dimethyl acetal and the resulting product of this reaction is heated with titanium tetrachloride in monoglyme to give 1-[4-bromo-α-(o-chlorophenyl)-o-tolyl]imidazole.

EXAMPLE 23

5-Propyl-1-[4-bromo-α-(o-chlorophenyl)-o-tolyl]imidazole

In the manner given in Example 3, 4-bromo-α-(o-chlorophenyl)-o-toluidine is reacted with triethyl orthoformate, the resulting oil is heated with 2-propyl-2-(aminomethyl)-1,3-dioxolane, and the resulting product treated with titanium tetrachloride to give 5-propyl-1-[4-bromo-α-(o-chlorophenyl)-o-tolyl]imidazole.

In the manner given in the preceding examples other 1-(α-phenyl-o-tolyl)imidazoles IV can be obtained.
Representative compounds thus obtained include:

1-(4-bromo-α-phenyl-o-tolyl)imidazole;
1-(5-bromo-α-phenyl-o-tolyl)imidazole;
4-methyl-1-(5-bromo-α-phenyl-o-tolyl)imidazole;
5-methyl-1-(5-bromo-α-phenyl-o-tolyl)imidazole;
4,5-dimethyl-1-(5-bromo-α-phenyl-o-tolyl)imidazole;
4-methyl-1-[α-(m-chlorophenyl)-o-tolyl]imidazole;
4-propyl-1-[α-(m-chlorophenyl)-o-tolyl]imidazole;
5-ethyl-4-propyl-1-[α-(m-chlorophenyl)-o-tolyl]imidazole;
4,5-dimethyl-1-[4-(trifluoromethyl)-α-(o-chlorophenyl)-o-tolyl]imidazole;
4,5-diethyl-1-[4-nitro-α-(o-chlorophenyl)-o-tolyl]imidazole;
5-propyl-1-(4-chloro-α-phenyl-o-tolyl)imidazole; and the like.

EXAMPLE 24

5-Chloro-2-(imidazol-1-yl)benzophenone

In a 500 ml. round bottom flask, 26.8 g. (0.100 mol) of 1-(4-chloro-α-phenyl-o-tolyl)imidazole is dissolved in 100 ml. of acetic acid. One hundred ml. of Jones' reagent is carefully added and the mixture is refluxed under nitrogen for 4 hours on a steam bath. After cooling to room temperature, the mixture is poured into 4.0 liter of cold 7% aqueous sodium hydroxide solution and extracted with 2.2 liter of chloroform. The chloroform extract is washed with aqueous saturated sodium chloride, dried over anhydrous magnesium sulfate, filtered, and concentrated to give a dark oil. This oil is dissolved in ethyl acetate, treated with 1.0 g. of activated charcoal, and filtered through anhydrous magnesium sulfate. Crystallization from ethyl acetate/hexane (½) affords 15.3 g. of 5-chloro-2-(imidazol-1-yl)benzophenone. Recrystallization of 1.0 g. of the product from ethyl acetate affords 0.30 g. of colorless prisms, of melting point 106°–108° C.

Anal. calcd. for $C_{16}H_{11}ClN_2O$:
C, 67.97; H, 3.92; N, 9.91; Cl, 12.54. Found: C, 67.78; H, 3.94; N, 9.97; Cl, 12.57.

EXAMPLE 25

2′,5-Dichloro-2-(imidazol-1-yl)benzophenone

In a 500 ml. round bottom flask 30.3 g. (0.100 mol) of 1-[4-chloro-α-(o-chlorophenyl)-o-tolyl]imidazole is dissolved in 100 ml. of acetic acid. One hundred ml. of Jones' reagent is added carefully and the mixture is refluxed under nitrogen for 4 hours on a steam bath. After cooling to room temperature, the mixture is poured into 4.0 l. of cold aqueous 7% sodium hydroxide solution and extracted with 2.2 l. of chloroform. The chloroform extract is washed with an aqueous saturated sodium chloride solution, dried over anhydrous magnesium sulfate and concentrated to an oil which crystallizes from ethyl acetate to afford 2′,5-dichloro-2-(imidazol-1-yl)benzophenone of melting point 146°–148° C.

Anal. calcd. for $C_{16}H_{10}Cl_2N_2O$, mw 317.17:
C, 60.59; H, 3.18; N, 8.83; Cl, 22.36. Found: C, 60.96; H, 3.38; N, 8.97; Cl, 22.26.

EXAMPLE 26

5-Chloro-2-(5-methylimidazol-1-yl)benzophenone

In the manner described in example 24, 5-methyl-1-(4-chloro-α-phenyl-o-tolyl)imidazole in acetic acid is treated with Jones' reagent and heated for 3 hours on a steam bath to give 5-chloro-2-(5-methylimidazol-1-yl)benzophenone.

EXAMPLE 27

2′,5-Dichloro-2-(5-methylimidazo-1-yl)-benzophenone

In the manner given in Example 24, 5-methyl-1-[4-chloro-α-(o-chlorophenyl)-o-tolyl]imidazole in acetic acid is heated with Jones' reagent to give 2′,5-dichloro-2-(5-methylimidazo-1-yl)benzophenone.

EXAMPLE 28

2′-Chloro-5-nitro-2-(imidazo-1-yl)benzophenone

In the manner given in Example 24, 1-[4-nitro-α-(o-chlorophenyl)-o-tolyl]imidazole in acetic acid is heated with Jones' reagent to give 2′-chloro-5-nitro-2-(imidazo-1-yl)benzophenone.

EXAMPLE 29

2'-Chloro-5-nitro-2-(5-methylimidazo-1-yl)-benzophenone

In the manner given in Example 24, 5-methyl-1-[4-nitro-α-(o-chlorophenyl)-o-tolyl]imidazole in acetic acid is heated with Jones' reagent to give 2'-chloro-5-nitro-2-(5-methylimidazo-1-yl)benzophenone.

EXAMPLE 30

2'-Chloro-5-fluoro-2-(imidazo-1-yl)benzophenone

In the manner given in Example 24, 1-[4-fluoro-α-(o-chlorophenyl)-o-tolyl]imidazole in acetic acid is heated with Jones' reagent to give 2'-chloro-5-fluoro-2-(imidazo-1-yl)benzophenone.

EXAMPLE 31

2'-Chloro-5-fluoro-2-(5-ethylimidazo-1-yl)-benzophenone

In the manner given in Example 24, 5-ethyl-1-[4-fluoro-α-(o-chlorophenyl)-o-tolyl]imidazole in acetic acid is heated with Jones' reagent to give 2'-chloro-5-fluoro-2-(5-ethylimidazo-1-yl)benzophenone.

EXAMPLE 32

5-(Trifluoromethyl)-2-(imidazo-1-yl)benzophenone

In the manner given in Example 24, 1-[4-(trifluoromethyl)-α-phenyl-o-tolyl]imidazole in acetic acid is heated with Jones' reagent to give 5-(trifluoromethyl)-2-(imidazo-1-yl)benzophenone.

EXAMPLE 33

5-(Trifluoromethyl)-2-(5-methylimidazo-1-yl)-benzophenone

In the manner given in Example 24, 5-methyl-1-[4-(trifluoromethyl)-α-(o-chlorophenyl)-o-tolyl]imidazole in acetic acid is heated with Jones' reagent to give 5-(trifluoromethyl)-2-(5-methylimidazo-1-yl)benzophenone.

EXAMPLE 34

5-Chloro-2',6'-difluoro-2-(imidazo-1-yl)benzophenone

In the manner given in Example 24, 1-[4-chloro-α-(2,6-difluorophenyl)-o-tolyl]imidazole in acetic acid is heated with Jones' reagent to give 5-chloro-2',6'-difluoro-2-(imidazo-1-yl)benzophenone.

EXAMPLE 35

5-Chloro-2',6'-difluoro-2-(4-ethyl-5-methylimidazo-1-yl)benzophenone

In the manner given in Example 24, 4-ethyl-5-methyl-1-[4-chloro-α-(2,6-difluorophenyl)-o-tolyl]imidazole in acetic acid is heated with Jones' reagent to give 5-chloro-2',6'-difluoro-2-(4-ethyl-5-methylimidazo-1-yl)-benzophenone.

EXAMPLE 36

5-Nitro-2-(imidazo-1-yl)benzophenone

In the manner given in Example 24, 1-(4-nitro-α-phenyl-o-tolyl)imidazole in acetic acid is heated with Jones' reagent to give 5-nitro-2-(imidazo-1-yl)benzophenone.

EXAMPLE 37

5-Nitro-2-(5-methylimidazo-1-yl)benzophenone

In the manner given in Example 24, 5-methyl-1-[4-nitro-α-phenyl-o-tolyl]imidazole in acetic acid is heated with Jones' reagent to give 5-nitro-2-(5-methylimidazo-1-yl)benzophenone.

EXAMPLE 38

5-Fluoro-2-(imidazo-1-yl)benzophenone

In the manner given in Example 24, 1-(4-fluoro-α-phenyl-o-tolyl)imidazole in acetic acid is heated with Jones' reagent to give 5-fluoro-2-(imidazo-1-yl)-benzophenone.

EXAMPLE 39

2'-Chloro-2-(imidazo-1-yl)benzophenone

In the manner given in Example 24, 1-[α-(o-chlorophenyl)-o-tolyl]imidazole in acetic acid is heated with Jones' reagent to give 2'-chloro-2-(imidazo-1-yl)-benzophenone.

EXAMPLE 40

2-(5-Methylimidazo-1-yl)benzophenone

In the manner given in Example 24, 5-methyl-1-(α-phenyl-o-tolyl)imidazole in acetic acid is heated with Jones' reagent to give 2-(5-methylimidazo-1-yl)benzophenone.

EXAMPLE 41

2'-Chloro-2-(5-methylimidazo-1-yl)benzophenone

In the manner given in Example 24, 5-methyl-1-[α-(o-chlorophenyl)-o-tolyl]imidazole in acetic acid is heated with Jones' reagent to give 2'-chloro-2-(5-methyl-imidazo-1-yl)benzophenone.

In the manner given in Example 24, other 2-(imidazol-1-yl)benzophenones can be produced. Representative products thus obtained include:

5-chloro-2'-fluoro-2-(imidazol-1-yl)benzophenone;
5-bromo-2'-chloro-2-(imidazol-1-yl)benzophenone;
2'-chloro-5-fluoro-2-(imidazol-1-yl)benzophenone;
4-chloro-2-(imidazol-1-yl)benzophenone;
3-(trifluoromethyl)-2-(imidazol-1-yl)benzophenone;
3'-chloro-2-(imidazol-1-yl)benzophenone;
5,4'-dichloro-2-(imidazol-1-yl)benzophenone;
5-bromo-2'-chloro-2-(5-methylimidazol-1-yl)benzophenone; 5-chloro-2'-fluoro-2-(5-methylimidazol-1-yl)benzophenone;
5-nitro-2'-fluoro-2-(5-ethylimidazol-1-yl)benzophenone;
5-nitro-2-(5-propylimidazol-1-yl)benzophenone;
5-fluoro-2-(5-isopropylimidazol-1-yl)benzophenone;
5-(trifluoromethyl)-2-(4,5-dimethylimidazol-1-yl)-benzophenone;
4-bromo-2'-chloro-2-(4,5-diethylimidazol-1-yl)benzophenone;
5-fluoro-2'-chloro-2-(4,5-dipropylimidazol-1-yl)benzophenone;
and the like.

I claim:
1. The compound of the formula IV:

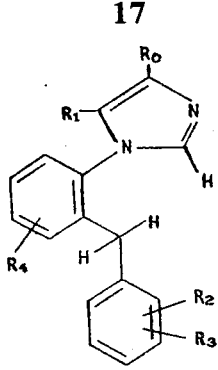

wherein $R_0$ and $R_1$ are hydrogen or alkyl of 1 to 3 carbon atoms, inclusive; wherein $R_2$ is hydrogen, fluoro, chloro, or trifluoromethyl; wherein $R_3$ is hydrogen or fluoro with the proviso that $R_3$ is not fluoro, if $R_2$ is chloro or trifluoromethyl; and wherein $R_4$ is hydrogen, fluoro, chloro, bromo, trifluoromethyl or nitro.

2. A compound according to claim 1 of the formula IVA:

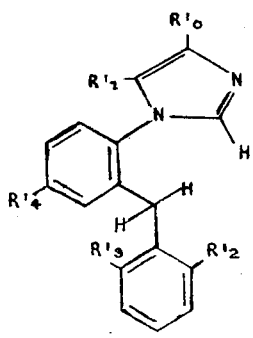

wherein $R_0'$ and $R_1'$ are hydrogen, methyl, or ethyl; wherein $R_2'$ is hydrogen, chloro, or fluoro; wherein $R_3'$ is hydrogen or fluoro with the proviso that $R_3'$ is not fluoro, if $R_2'$ is chloro; and wherein $R_4'$ is hydrogen, fluoro, chloro, or trifluoromethyl.

3. A compound according to claim 1 of the formula IVB:

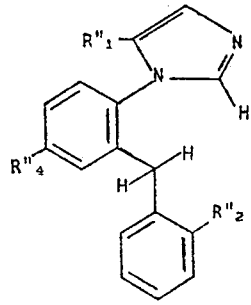

wherein $R_1''$ is hydrogen or methyl; wherein $R_2''$ is hydrogen of chloro; wherein $R_4''$ is hydrogen, chloro, or fluoro.

4. A compound according to claim 3 wherein $R_1''$ and $R_2''$ are hydrogen, $R_4''$ is chloro and the compound is therefore 1-(4-chloro-α-phenyl-o-tolyl)imidazole.

5. A compound according to claim 3, wherein $R_1''$ is hydrogen, $R_2''$ and $R_4''$ are chloro and the compound is therefore 1-[4-chloro-α-(o-chlorophenyl)-o-tolyl]imidazole.

6. A compound according to claim 3, wherein $R_1''$ is methyl, $R_2''$ is hydrogen, $R_4''$ is chloro and the compound is therefore 5-methyl-1-(4-chloro-α-phenyl-o-tolyl)-imidazole.

7. A compound according to claim 3, wherein $R_1''$ and $R_4''$ are hydrogen; $R_2''$ is chloro and the compound is therefore 1-[α-(o-chlorophenyl)-o-tolyl]imidazole.

8. A compound according to claim 3, wherein $R_1''$ and $R_2''$ are hydrogen, $R_4''$ is fluoro and the compound is therefore 1-(4-fluoro-α-phenyl-o-tolyl)imidazole.

9. A compound according to claim 3, wherein $R_1''$ is methyl, $R_2''$ and $R_4''$ are chloro and the compound is therefore 5-methyl-1-[4-chloro-α-(o-chlorophenyl)-o-tolyl]imidazole.

10. A compound according to claim 2, wherein $R_1'$, $R_0'$, and $R_3'$ are hydrogen, $R_2'$ is fluoro, $R_4'$ is chloro and the compound is therefore 1-[4-chloro-α-(o-fluorophenyl)-o-tolyl]imidazole.

11. A compound according to claim 1, wherein $R_1$ is methyl, $R_0$, $R_2$, and $R_3$ are hydrogen, $R_4$ is 4-nitro and the compound is therefore 5-methyl-1-(4-nitro-α-phenyl-o-tolyl)imidazole.

12. A compound according to claim 2, wherein $R_4'$ is trifluoromethyl, $R_1'$ is methyl, $R_0'$, $R_2'$, and $R_3'$ are hydrogen and the compound is therefore 5-methyl-1-[4-(trifluoromethyl)-α-phenyl-o-tolyl]imidazole.

* * * * *

UNITED STATES PATENT AND TRADEMARK OFFICE
CERTIFICATE OF CORRECTION

PATENT NO. : 3,992,400
DATED      : November 16, 1976
INVENTOR(S) : Martin Gall

It is certified that error appears in the above-identified patent and that said Letters Patent are hereby corrected as shown below:

Column 17, line 43: "$R_0$'" should read -- $R'_0$ --
line 43: "$R_1$'" should read -- $R'_1$ --
line 44: "$R_2$'" should read -- $R'_2$ --
line 44: "$R_3$'" should read -- $R'_3$ --
line 45: "$R_3$'" should read -- $R'_3$ --
line 46: "$R_3$'" should read -- $R'_3$ --
line 46: "$R_4$'" should read -- $R'_4$ --

Signed and Sealed this

Twenty-sixth Day of June 1979

[SEAL]

Attest:

RUTH C. MASON
Attesting Officer

DONALD W. BANNER
Commissioner of Patents and Trademarks